United States Patent [19]

Garelli-Calvet et al.

[11] Patent Number: 5,403,922

[45] Date of Patent: Apr. 4, 1995

[54] AMPHIPHILIC COMPOUNDS CONTAINING TWO SUGAR OR SUGAR-DERIVED HEAD GROUPS

[76] Inventors: Rachel Garelli-Calvet, 3 rue du Four, 31380 Montastruc La Conseillere; Florence Brisset, 4 rue Rene Leduc, 31130 Balma; Isabelle Rico; Armand Lattes, both of 8 residence des Jardins Occitans, 31520 Ramonville; Lionel Godefroy, 32 rue Victor Hugo, 38430 Moirans, all of France

[21] Appl. No.: 255,109

[22] Filed: Jun. 7, 1994

Related U.S. Application Data

[63] Continuation of Ser. No. 971,347, Nov. 4, 1992, abandoned.

[30] Foreign Application Priority Data

Nov. 5, 1991 [FR] France .................. 91 13851

[51] Int. Cl.$^6$ ............... C07H 15/02; A61K 9/133; B01F 17/56
[52] U.S. Cl. .................. 536/1.11; 536/4.1; 536/17.6; 536/22.1; 536/54; 536/122; 536/124
[58] Field of Search ............ 536/1.11, 4.1, 17.6, 536/22.1, 54, 122, 124; 514/23, 25, 42

[56] References Cited

U.S. PATENT DOCUMENTS

| | | | |
|---|---|---|---|
| 3,855,290 | 12/1974 | Zak et al. | 8/127.6 |
| 4,234,572 | 11/1980 | Petersen et al. | 536/16.8 |
| 4,258,034 | 3/1981 | Joseph et al. | 514/25 |
| 5,200,398 | 4/1993 | Strasberg et al. | 514/23 |

FOREIGN PATENT DOCUMENTS

| | | |
|---|---|---|
| 0312087A2 | 4/1989 | European Pat. Off. . |
| 0447064A2 | 9/1991 | European Pat. Off. . |
| 2235113 | 1/1975 | France . |

OTHER PUBLICATIONS

Menger and Wrenn, 1976, J. Phys. Chem 80: (24) 2651 "Interfacial and Micellar Properties of Bolaform Electrolytes".
Fuhrhop et al., 1986, J. Am. Chem. Soc. 108: 1785 "Bloaamphiphiles and Monolayer Lipid Membranes Made From 1,6,19,24-Tetraoxa-3,21-cyclohexatriacontadiene-2,5,20,23-tetrone".
Tschierske and Zaschke, 1990, J. Chem. Soc. Chem. Commun. p. 1013 "Novel Thermotropic and Lyotropic Double Headed Diol-based Mesogens".
Emmerling et al, 1981, Starch [Iacuna] 33: (6) 202-208 "Preparative Methods for the Preparation of Higher Maltooligomers and their Coupling with Aliphatic Diamines".
Furhop et al., 1984, Angewandte Chemie 23: 100-113 "Routes to Functional Vesicle Membranes Without Proteins".
Hjelmeland, et al., Analytical Biochem., 1983 130: 485-490. "A New Class of Nonionic Detergents with a Gluconamide Polar Group".

*Primary Examiner*—Ronald W. Griffin
*Attorney, Agent, or Firm*—Allegretti & Witcoff, Ltd.

[57] ABSTRACT

The subject of the invention is a surface-active composition, comprising a bolaamphiphile or bolaform chemical compound, containing a linear or branched, hydrophobic carbon chain at the two ends of which are arranged two hydrophilic portions or head group groups, corresponding to the following general formula:

R A E A R in which:
E represents the carbon chain, containing at least six carbon atoms, optionally interrupted by at least one aromatic, or heterocyclic, or functional group
A is a bonding functional group
R is a residue of a reducing glucide containing a linear or cyclized chain, or of a derivative of the said glucide, bonded directly or indirectly via one of its aldehyde or ketone functional groups, or derived functional group, to the functional group A.

The invention also relates to their applications as components of surface-active agents and vesicular agents, and to a process for their preparation.

16 Claims, No Drawings

AMPHIPHILIC COMPOUNDS CONTAINING TWO SUGAR OR SUGAR-DERIVED HEAD GROUPS

This is a continuation of Ser. No. 07/971,347, filed on Nov. 4, 1992, now abandoned.

The invention relates to new compounds called bolaamphiphile or bolaform compounds, having surface-active properties, and which can be used especially as vesicular agents.

Bolaamphiphile or bolaform compounds are understood to mean any compound containing:

a relatively long, linear or branched, and hydrophobic carbon chain, optionally with hetero atoms and two polar parts or hydrophilic head groups, respectively arranged at and covalently bonded to the two ends of the carbon chain.

The term "bolas" derives from a South American weapon consisting of two balls joined by a rope or a leather thong.

Various natural bolaform compounds are already known and constitute the lipid membrane of bacteria called Archaebacteria; cf. T. D. Brock, La Recherche, 1988, 19 (198), 478.

The generally surface-active bolaform compounds make it possible to form aggregates of the cylindrical micellar type or, at higher concentrations, of lyotropic liquid crystals (lameliar, hexagonal phases). These various aggregates are obtained, by processes which are still little understood, from at least one double layer of the bolaform compound, itself obtained from a two-phase water/bolaform compound solution, often with an energy input, for example ultrasound.

Various bolaform compounds have already been obtained and studied, namely:

compounds with quaternary ammonium head groups, (cf. F. M. Manger and S. Wrenn, J. Phys. Chem., 1976, 80, (24), 2651), optionally with two relatively long carbon chains between the two hydrophilic head groups, (cf. J-H. Fuhrhop, et al., J. Am. Chem. Soc., 1986, 108, 1785)

compounds with identical or non-identical anionic head groups of the sulfate or carboxylate type, separated by one or two hydrocarbon chains (cf. J-H. Fuhrhop, et al., J. Am. Chem. Soc., 1986, 108, 1785)

compounds with identical or non-identical nonionic head groups of the polyol type (cf. for example, C. Tschierske and H. Zaschke, J. Chem. Soc., Chem. Commun., 1990, 1013)

and, finally, symmetrical compounds with two head groups of compounds, which head groups are derived from sugar and are joined to each other by two hydrocarbon chains, each head group consisting of a thioglucoside or thiogalactoside residue, bonded by the sulfur atom to the skeleton comprising the two hydrocarbon chains, (cf. J-H. Fuhrhop, et al., J. Am. Chem. Soc., 1986, 108, 1785).

The synthesis of these compounds involves several successive stages, with relatively low yields for some of them, which makes such compounds unsuitable for industrial production.

Various documents have already described compounds comprising a relatively long carbon chain, with two sugar or sugar-derived parts, covalently bonded respectively to the two ends of the carbon chain, but without revealing any surface-active properties linked to these compounds:

document EP-A-0,447,064 describes, as softening agent in a cosmetic composition, N,N'-dilactobionamidoalkanes comprising:
 * a carbon chain having from 2 to 14 carbon atoms,
 * two glycoside residues, each comprising from 1 to 5 carbon atoms, bonded by their aldehyde or ketone functional groups respectively to the two ends of the carbon chain via a tertiary amine functional group;

softening properties do not infer surface-active properties, especially detergent properties, since these softening agents are intended, in particular, to combat the drying effects of common surface-active agents;

document EP-A-0,312,087 describes, as intermediates for organic synthesis, N,N'-digluconamidoalkanes especially comprising:
 * a carbon chain having from 2 to 22 carbon atoms, optionally substituted by one or more ester functional groups, and optionally interrupted by one or more groups such as O, S or S—S,
 * and two gluconamide parts, each substituted once by a monosaccharide or polysaccharide residue, covalently bonded respectively to the two ends of the carbon chain;

document FR-A-2,235,113 describes, as emollient in a cosmetic composition, and in the salt form, compounds comprising:
 * an unsaturated carbon chain having from 2 to 6 carbon atoms,
 * two glucose residues, bonded by their ketone functional group, via a diamino functional group, respectively to the two ends of the carbon chain;

emollient properties do not necessarily infer surface-active properties and can be introduced via products which are very different from detergents, such as oils;

and, finally, document "Starch [lacuna], Vol. 33, No. 6, June 1981, pages 202–208, explores various ways of preparing oligosaccharides and polysaccharides, coupled respectively to the two ends of aliphatic diamines; this is a scientific study which has not revealed particularly useful properties of the compounds thus prepared.

The subject of the present invention is thus new bolaform compounds, containing two sugar or sugar-derived head groups, which compounds can be obtained in one, or two stages, at the most with acceptable yields and which can, for this reason, be produced on an industrial scale.

A composition according to the present invention contains a bolaformcompound corresponding to the following general formula:

RAEAR in which:

E represents a carbon chain, containing at least six carbon atoms, optionally interrupted by at least one aromatic, or heterocyclic, or functional group A is a bonding functional group R is a residue of a reducing glucide containing a linear or cyclized chain, or of a derivative of the said reducing glucide, bonded directly or indirectly (for example, via an alkyl chain) via one of its aldehdye or ketone, or derived (for example, amide) functional groups, to the functional group A.

Besides their surface-active properties, and especially their vesicular properties, the bolaform compounds according to the present invention have the determining advantage of being able to be synthesized directly by condensation between an acid form of the monosaccharide (for example, gluconic acid), or of the polysaccharide (for example, lactobionic acid), [lacuna] without passing through the lactone or internal ester form of the same saccharide, as recommended by certain documents of the prior art.

One of the main advantages of the compositions of the present invention is provided by their behavior in aqueous solution, and relates to their application as surface-active agent. The field of these applications is all the wider since these compositions have no or very little toxicity, which makes it possible to envisage their use in cosmetics, pharmaceuticals, and the like.

Their behavior in aqueous solution confers particularly advantageous properties on them, in that they can directly form vesicular structures.

This property makes it possible to use the compounds according to the invention as encapsulating agents, but also for the extraction of membranous proteins, in immunology, and the like.

Additionally, the invention makes it possible to provide bolaform compounds which have optical isomerism properties, the two hydrophilic parts being chiral. The compounds of the invention can then be used as asymmetry inductors.

An advantageous bolaformcompound of the present invention comprises a linear and saturated, hydrophobic carbon chain.

Advantageously, the number of carbon atoms of the carbon chain of the bolaform compound is between 6 and 24 carbon atoms and preferably between 6 and 14.

The functional group A of the bolaform compound is chosen especially from the group comprising the functional groups:

O, OCO, S, NH, NHCO, the OCO functional groups comprising the expanded formulae:

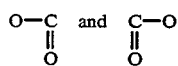

and NHCO comprising the expanded formulae:

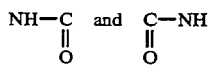

Preferably, the functional group A is the amine functional group NH.

The reducing glucide of the residue R of the bolaform compound is a monosaccharide or a polysaccharide.

Among the preferred monosaccharides, the reducing glucide is chosen from the group comprising glucose and galactose.

Among the polysaccharides, the disaccharides are preferred, and especially those chosen from the group comprising lactose, cellobiose and maltose.

Another family of bolaformcompounds according to the present invention is obtained, by choosing:

the NHCO and/or CONH functional group as bonding functional group A and a gluconamide as derivative of a reducing glucide, bonded via its amide functional group, via an alkyl chain containing from two to six carbon atoms, to the bonding functional group A.

The expanded formula of these compounds is:

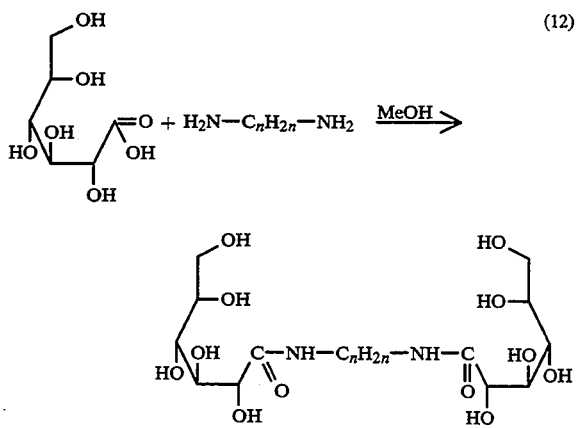

(12)

They can be obtained by directly reacting gluconic acid, an akyldioic acid and a diaminoalkane.

Another family of bolaformcompounds according to the present invention is obtained, by choosing:

the NH functional group as bonding functional group A a carbon chain E interrupted by one or more NH functional groups and a reducing glucide consisting of a disaccharide, for example lactose.

Examples of this family are bislactobionamidospermidines and bislactobionamidospermines.

Another family of bolaformcompounds according to the present invention is obtained, by choosing:

the NH functional group as bonding functional group A a chain E interrupted by one or more O functional groups and a reducing glucide consisting of a monosaccharide, such as glucose, or a disaccharide, for example lactose.

Examples of this family are bisgluconamidodioxo[lacuna] or trioxoalkanes and bislactobionamidodioxo[lacuna] or trioxoalkanes.

Another family of bolaformcompounds according to the present invention is obtained, by choosing:

the NH functional group as bonding functional group A and a reducing glucide consisting of a monosaccharide or polysaccharide, containing an oxygen-containing heterocycle, or a derivative (for example, aminated) of the said glucide.

Examples of this family are bisaminolactose alkanes or bisglucosaminoalkanes.

Another subject of the invention is a process for preparing such amphiphilic compounds.

This process consists in directly reacting an oxidized, or reduced, or aminated reactive form of the reducing glucide of the residue R with a product corresponding to the formula B E B, E being the hydrophobic carbon chain described above, and B corresponding to the functional group A before condensation with the reactive form of the glucide.

The reaction is preferably carried out in an alcoholic solvent, and especially in methanol.

Depending on the starting material, the reaction can take place at room temperature with stirring or else the reaction mixture has to be heated and especially to the reflux temperature of the solvent.

Depending on the operating conditions, the best reaction yield is obtained with reaction times of between 12 and 48 hours, and preferably of 24 hours.

To prepare a compound of the invention, the oxidized starting form chosen can be the lactone form or the acid form; preferentially, the acid form will be chosen.

Thus, to prepare a compound for which R is a glucose residue, gluconolactone can be chosen to react with the product B E B.

To prepare a compound for which R is a lactose residue, lactobionic acid can be chosen to react with the product B E B.

The bolaform compounds of the invention, an application and a preparation process are detailed below with the following Examples 1 to 12.

In the following examples, the microanalyses of the compounds prepared were carried out using a Technicon apparatus.

The NMR analyses were carried out on a Brucker AC200 spectrophotometer at 200.13 MHz for $^1$H NMR and at 50.32 MHz for $^{13}$NMR.

The $^1$H and $^{13}$C NMR spectra were recorded in DMSO.

Example 1:1,12-Digluconamidododecane 0.56 g of 1,12-diaminododecane is added to a solution containing 1 g of gluconolactone and 50 ml of methanol. The reaction mixture is stirred for 24 hours at room temperature. The 1,12-digluconamidododecane bolaamphiphile derivative precipitates in the mixture and is filtered. The solid obtained is dried and then lyophilized.

1.38 g of solid white product is obtained, analysis of which shows that it is the compound of formula:

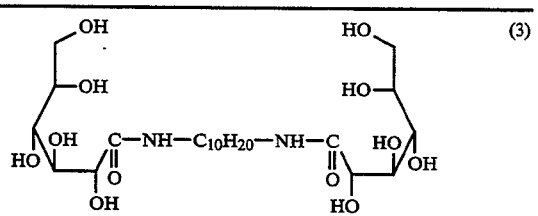

| Microanalyses | % C | % H | % N | % O |
| --- | --- | --- | --- | --- |
| Calculated | 51.8 | 8.7 | 5.0 | 34.5 |
| Found | 51.2 | 8.7 | 5.0 | 34.2 |

Example 2:1,10-Digluconamidodecane

The procedure is the same as in Example 2 [sic], using 1 g of gluconolactone and 0.48 g of 1,10-diaminodecane.

1.28 g of product are recovered, analysis of which shows that it is the product of formula:

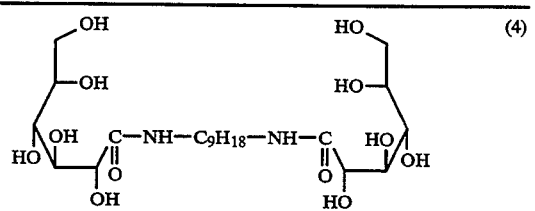

| Microanalyses | % C | % H | % N | % O |
| --- | --- | --- | --- | --- |
| Calculated | 50.0 | 8.4 | 5.3 | 36.3 |
| Found | 49.5 | 8.4 | 5.3 | 36.8 |

Example 3:1,9-Digluconamidononane

The procedure is the same as in the above examples using 1 g of gluconolactone and 0.45 g of 1,9-diaminononane.

1.30 g of product is recovered, analysis of which shows that it is the product of formula:

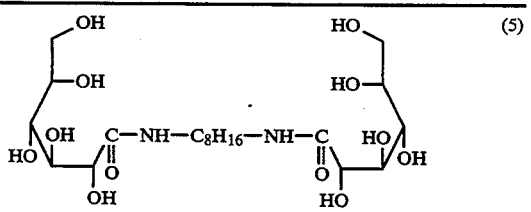

| Microanalyses | % C | % H | % N | % O |
| --- | --- | --- | --- | --- |
| Calculated | 49.0 | 8.3 | 5.4 | 37.3 |
| Found | 48.9 | 8.5 | 5.4 | 37.1 |

Example 4:1,8-Digluconamidooctane

The procedure is the same as in the above examples using 1 g of gluconolactone and 0.41 g of 1,8-diaminooctane.

1.20 g of product is recovered, analysis of which shows that it is the product of formula:

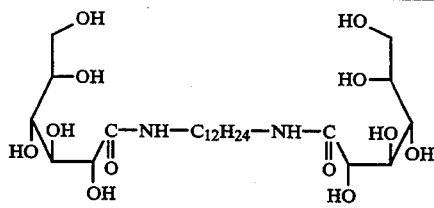

| Microanalyses | % C | % H | % N | % O |
| --- | --- | --- | --- | --- |
| Calculated | 48.0 | 8.1 | 5.6 | 38.3 |
| Found | 48.0 | 8.1 | 5.6 | 38.3 |

Example 5:1,7-Digluconamidoheptane

The procedure is the same as in the above examples using 1 g of gluconolactone and 0.37 g of 1,7-diaminoheptane.

1.07 g of product is recovered, analysis of which shows that it is the product of formula:

| Microanalyses | % C | % H | % N | % O |
|---|---|---|---|---|
| Calculated | 46.9 | 7.9 | 5.8 | 39.5 |
| Found | 46.6 | 7.9 | 5.6 | 39.9 |

Example 6: 1,6-Digluconamidohexane

The procedure is the same as in the above examples using 1 g of gluconolactone and 0.33 g of 1,6-diaminohexane.

1.18 g of product is recovered, analysis of which shows that it is the product of formula:

| Microanalyses | % C | % H | % N | % O |
|---|---|---|---|---|
| Calculated | 45.7 | 7.7 | 5.9 | 40.6 |
| Found | 46.1 | 7.8 | 5.9 | 40.2 |

NMR:

Alkyl chain: $-\text{NH}-\overset{\alpha}{\text{CH}_2}-\overset{\beta}{\text{CH}_2}-\overset{\gamma}{\text{CH}_2}-\overset{\gamma}{\text{CH}_2}-\overset{\beta}{\text{CH}_2}-\overset{\alpha}{\text{CH}_2}-\text{NH}-$ $^{13}$C NMR:

Alkyl chain: $\overset{\gamma}{\text{CH}_2}$(25.98), $\overset{\beta}{\text{CH}_2}$(29.01), $\overset{\alpha}{\text{CH}_2}$(38.12), Sugar portion:
C$_6$
C$_2$, C$_3$, C$_4$, C$_5$ (70.04, 71.40, 72.33, 73.55)
C$_1$ (172.18)
$^1$H NMR:

$\overset{\gamma}{}$
1.25 ppm (4p, m, 2CH$_2$)

$\overset{\beta}{}$
1.41 ppm (4p, m, 2CH$_2$)

$\overset{\alpha}{}$
3–6 ppm (26p, m, CHOH, CH$_2$OH, CH$_2$—NH—C=O)
7.60 ppm (2p, t, 2NH)

Example 7: 1,12-Dilactobionamidododecane 0.26 g of 1,12-diaminododecane is added to a solution of lactobionic acid (1 g) in 100 ml of methanol. The reaction mixture is stirred for 24 hours at methanol reflux. The solvent is evaporated under vacuum and the product is then lyophilized.

1.16 g of solid product is obtained, analysis of which shows that it is the compound of formula:

The microanalyses of the lactose derivatives are not shown because the products are very hygroscopic.

Example 8: 1,10-Dilactobionamidodecane

The procedure is the same as in Example 7 using 1 g of lactobionic acid and 0.23 g of 1,10-diaminodecane.

1.10 g of product is recovered, analysis of which shows that it is the product of formula:

Example 9: 1,9-Dilactobionamidononane

The procedure is the same as in the above examples using 1 g of lactobionic acid and 0.21 g of 1,9-diaminononane.

1.08 g of product is recovered, analysis of which shows that it is the product of formula:

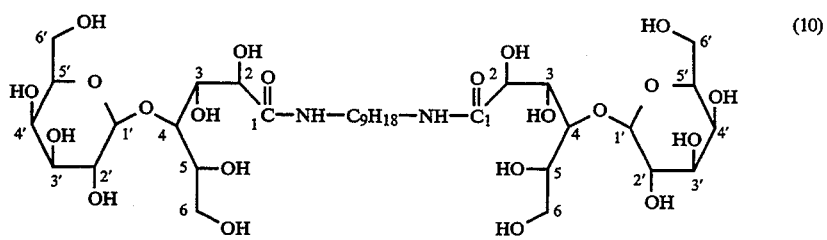

(10)

NMR:

Alkyl chain: $\underset{\alpha}{-NH}-\underset{\beta}{CH_2}-\underset{\gamma}{CH_2}-\underset{\delta}{CH_2}-\underset{\epsilon}{CH_2}-\underset{\epsilon}{CH_2}-\underset{\delta}{CH_2}-\underset{\gamma}{CH_2}-\underset{\beta}{CH_2}-\underset{\alpha}{CH_2}-NH-$ $^{13}C$ NMR:

Alkyl chain: $\underset{\epsilon}{CH_2(26.50)}$, $\underset{\delta}{CH_2(28.72)}$, $\underset{\gamma}{CH_2(28.93)}$, $\underset{\beta}{CH_2(29.14)}$, $\underset{\alpha}{CH_2(38.16)}$ Sugar portion:
$C_6$ and $C_6$ [sic], (60.59, 62.27)
$C_2$, $c_2'$ [sic], $C_3$, $C_3'$, $C_4$, $C_4'$, $C_5$, $C_5'$ (68–83 ppm)
$C_1$ (171.97)
$C_1'$ (104.54)

$^1H$ NMR:
1.24 ppm (10p, m, $5CH_2$)
1.40 ppm (4p, m, $2CH_2$)
3–6 ppm (46p, m, CHOH, $CH_2OH$, $CH_2-NH-C=O$, CH—O)
7.57 ppm (2p, t, 2NH)

Example 10: 1,8-Dilactobionamidooctane

The procedure is the same as in the above examples using 1 g of lactobionic acid and 0.19 g of 1,8-diaminooctane.

1.06 g of product is recovered, analysis of which shows that it is the product of formula:

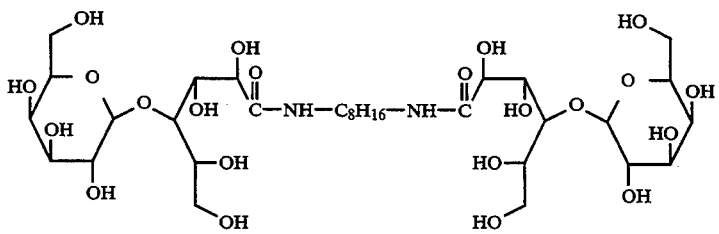

(11)

Example 11

The surface-active properties in aqueous solution of 1,8-digluconamidooctane and 1,8-dilactobionamidooctane prepared respectively according to Examples 4 and 10 can be measured using conventional techniques for measuring surface tension with a Tensimat N3 tensiometer (Prolabo, France). The moving part providing the measurement is a caliper provided with the apparatus formed from a platinum wire which is 0.1 mm in diameter and 2 cm in length (distance between the two branches of the caliper). The results are illustrated in Tables I and II showing the surface tensions at varying concentrations of bolaamphiphile derivatives (in Table I with 1,8-digluconamidooctane and in Table II with 1,8-dilactobionamidooctane).

TABLE I

| Surface-active power of 1,8-digluconamidooctane at 40° C. | |
|---|---|
| Concentration | ST (mN/m) |
| $2 \times 10^{-2}$ M | 46.6 |
| $10^{-2}$ M | 54.8 |

TABLE I-continued

| Surface-active power of 1,8-digluconamidooctane at 40° C. | |
|---|---|
| Concentration | ST (mN/m) |
| $5 \times 10^{-3}$ M | 58.4 |
| $10^{-3}$ M | 60.6 |
| $5 \times 10^{-4}$ M | 68.9 |

TABLE II

| Surface-active power of 1,8-dilactobionamidooctane at 40° C. | |
|---|---|
| Concentration | ST (mN/m) |
| $2 \times 10^{-2}$ M | 54.9 |
| $10^{-2}$ M | 59.6 |
| $5 \times 10^{-3}$ M | 67 |

Example 12

Examination by light diffusion (using a Coulter apparatus, mode N4MD) of 1,8-digluconamidooctane and 1,8-dilactobionamidooctane solutions in a range of concentrations which can vary from $10^{-3}$ M to $5.10^{-2}$ M makes it possible to reveal the existence of aggregates with a maximum size of 1000 nm.

An electron microscope study shows that these aggregates are unilamellar vesicles. The procedure of this study can be briefly described thus: a few drops of the bolaamphiphile solution (which may or may not be subjected to ultrasound) are applied to a copper grid (150 mesh) covered with a carbon film. The deposit is then dried. A 2% uranyl acetate solution in water is then deposited in the Same way on the grid.

The photographs of these samples obtained using an electron microscope (Phillips EM 301) show:
for 1,8-digluconamidooctane at a concentration of 0.007 mol/l vesicles of 165 nm and 325 nm (magnification ×42000)
for 1,8-dilactobionamidooctane at a concentration of 0.02 mol/l vesicles of 125 nm, 280 nm and 375 nm (magnification ×32000).

Other bolaamphiphile or bolaform surface-active compounds containing two sugar-derived head group groups were synthesized, namely the five following chemical families:

1-bis[lacuna] or digluconamidoalkanes and bis[-lacuna] or dilactobionamidoalkanes, prepared according to a process other than that in Examples 1 to 10.

2-bis[lacuna] or dilactobionamidospermidine and spermine[lacuna].

3-bis[lacuna] or digluconamidodioxo- or trioxoalkanes and bis[lacuna] or dilactobionamidodioxo- or trioxoalkanes.

4-bis[lacuna] or diaminolactose alkanes.

5-bis[lacuna] or diglucosaminoalkanes.

These families of bolaform surface-active agents were synthesized according to a single-stage procedure, without prior protection of the sugar portions.

1-Bisgluconamido- and bislactobionamidoalkanes a) Bisgluconamidoalkanes

The method of synthesis consists in reacting one equivalent of diamine containing a long alkyl chain with two equivalents of gluconic acid in methanol according to the following reaction scheme:

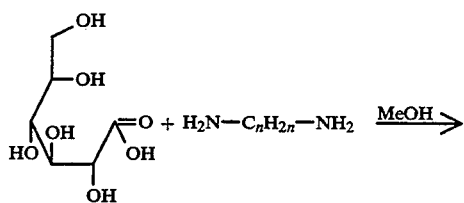

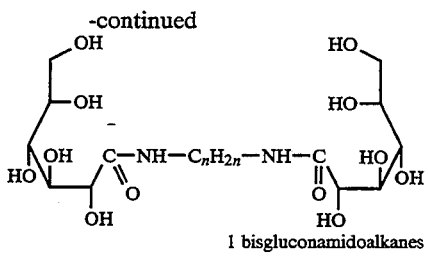

1 bisgluconamidoalkanes

The reaction mixture is kept stirring at room temperature for 24 hours. The reaction product precipitates. It is recovered by filtering and is washed while hot with methanol to remove possible traces of unreacted diamine.

The yields, as isolated products, are collated in the following table:

| Preparative yields of bisgluconamides | | |
|---|---|---|
| Derivatives | n | Yields (%) |
| 1a | 6 | 90 |
| 1b | 7 | 83 |
| 1c | 8 | 85 |
| 1d | 9 | 90 |
| 1e | 10 | 86 |
| 1f | 12 | 88 |

The products obtained are in the form of a white powder; they were characterized by mass spectrometry, $H^1$ and $^{13}C$ NMR and microanalysis.

b) Bislactobionamidoalkanes

Bislactobionamidoalkanes are synthesized from two equivalents of lactobiolnic acid and one equivalent of diamine containing a long alkane chain in methanol according to the following reaction scheme:

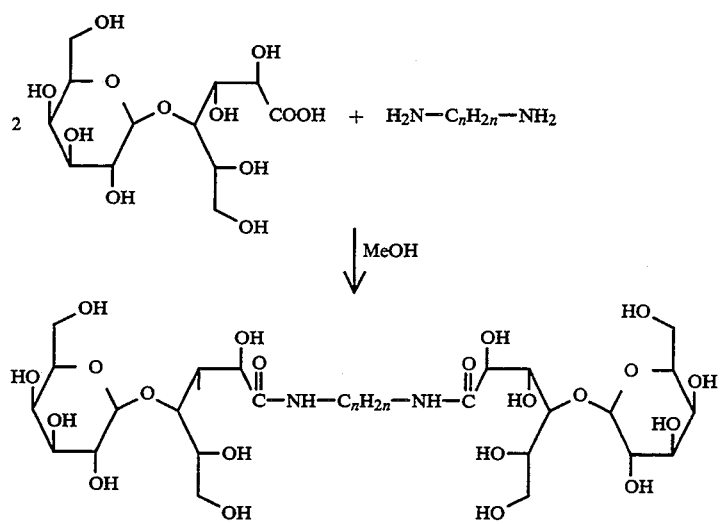

2 bislactobionamidoalkanes

The diamine reacts with the lactone formed in situ in the methanol. The reaction mixture is kept stirring for 24 hours at methanol reflux.

The more hydrophilic product does not precipitate. The solvent is therefore evaporated under vacuum and the product is lyophilized.

The reaction yields are quantitative. They are collated in the following table:

| Preparative yields of bislactobionamides | | |
|---|---|---|
| Derivatives | n | Yields (%) |
| 2a | 6 | 100 |
| 2b | 7 | 100 |
| 2c | 8 | 100 |
| 2d | 9 | 100 |
| 2e | 10 | 100 |
| 2f | 12 | 100 |

The derivatives obtained were characterized by microanalysis, $H^1$ and $^{13}C$ NMR and mass spectrometry.

2- Bislactobionamidospermidine and bislactobionamidospermine

These bolaform compounds were synthesized from biological diamines, spermidine and spermine, with the following respective formulae:

$H_2N-(CH_2)_4-NH-(CH_2)_3-NH_2$   3

$H_2N-(CH_2)_3-NH-(CH_2)_4-NH-(CH_2)_3-NH_2$   4

Bislactobionamidospermidine 3 and bislactobionamidospermine 4 are synthesized from 2 equivalents of lactobionic acid and one equivalent of diamine, in a water/2-propanol mixture or methanol. The reaction is carried out for 24 hours at room temperature. The solvent is then evaporated under vacuum and the products are lyophilized.

The reaction yields as well as the procedures are combined in the following table:

| Preparative yields and solvents used for the synthesis of bislactobiospermidine 3 and bislactobiospermine 4 | | |
|---|---|---|
| Derivatives | Solvent | Yields (%) |
| 3 | water/2-propanol | 90 |
| 4 | methanol | 100 |

These derivatives exist in the form of a white hydroscopic powder. They were characterized by $H^1$ and $^{13}C$ NMR and microanalysis.

3-Bisgluconamidodioxo[lacuna] or trioxoalkanes and bislactobionamidodioxo[lacuna] or trioxoalkanes For the purpose of functionalizing the hydrophobic chain of the bolaforms, diamines were used containing long oxygenated chains.

The general formula of these diamines is the following:

$H_2N-(CH_2)_n-O-(CH_2)_m-O-(CH_2)_p-(O-(CH_2)_r)_s-NH_2$

The various diamines will be identified by the following code:

n—O—m—O—p—(O—r)$_s$

The oxygenated diamines used will thus be:

30203(s=0)

30603 (s=0)

3020203 (s=1, r=3)

a) Bisgluconamidodioxo[lacuna] or trioxoalkanes

The various amines were added to the gluconic acid in ½ respective proportions. The solvent used varies depending on the diamines used.

The operating conditions, as well as the yields, are collated in the following table:

| Procedures and yields in the preparation of bisgluconamidodioxo[lacuna] or trioxoalkanes | | | | |
|---|---|---|---|---|
| Derivatives | Diamines | Solvent | Operating conditions | Yield (%) |
| 5a | 30203 | methanol | - 24 h at room temp. | 67 |
| 5b | 30603 | 2 propanol | - filtration of the product obtained | 53 |
| 5c | 3020203 | 2 propanol | - lyophilization | 60 |

The products obtained exist in the form of a hygroscopic white powder and have the following formula:

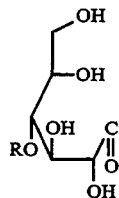 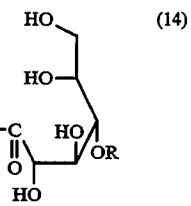 (14)

$C-NH-(CH_2)_n-O-(CH_2)_m-O-(CH_2)_p-(O-(CH_2)_r)_s-NH-C$ 5 (R = H) bisgluconamidotrioxo[lacuna] or dioxoalkanes 5 (R=H) bisgluconamidotrioxo[lacuna] or dioxoalkanes They were characterized by $H^1$ nad $^{13}C$ NMR and microanalysis.

b) Bislactobionamidodioxo[lacuna] or trioxoalkanes

Lactobionic acid in aqueous solution is added to the oxygenated diamine in solution in 2-propanol.

As above, the operating conditions vary depending on the diamines used. The operating conditions, as well as the reaction yields, are combined in the following table:

| Operating conditions and yields in the synthesis of bislactobionamidodioxo[lacuna] or trioxoalkanes 6 | | | | |
|---|---|---|---|---|
| Derivatives | Diamines | Solvent | Operating conditions | Yield (%) |
| 6a | 30203 | water/2 propanol[sic] | - 9h 30 at 70° C. - 14h 30 at room temperature | 100 |
| 6b | 30603 | (1/1) | - evaporation of the solvent - lyophilization | 100 |
| 6c | 3020203 | | - 3h 30 at 70° C. - 16h 30 at room temperature - evaporation of the solvent | 100 |

-continued

Operating conditions and yields in the synthesis of bislactobionamidodioxo[lacuna] or trioxoalkanes 6

| Derivatives | Diamines | Solvent | Operating conditions | Yield (%) |
|---|---|---|---|---|
| | | | - lyophilization | |

Bislactobionamidodioxo[lacuna] or trioxoalkanes have the same formula as above (cf. compound 5) but here R=galactose (compound 6).

These products are very hygroscopic and they must be stored under an inert atmosphere. They were characterized by $H^1$ and $^{13}C$ NMR and microanalysis.

4- Bisaminolactose alkanes

Thus far, the bolaform compounds synthesized contain an open glucose ring. It seemed advantageous to synthesize bolaform compounds whose glucose ring stays closed.

The synthesis of the following bolaforms was thus attempted:

(15)

7 bisaminolactose alkanes

7 Bisamonolactose alkanes R=galactose

The synthesis (n=12) is carried out in a single stage: the lactose, in aqueous solution, is added to the diamine in solution in 2-propanol. Reaction is carried out for 24 hours. The product is purified by recrystallization. The reaction yield is 70%.

The product was characterized by $H^1$ and $^{13}C$ NMR and microanalysis.

5 - Bisglucosaminoalkanes

As above, the advantage of synthesizing bolaform compounds from glucosamine is the preservation of the pyranosyl ring and additionally of its anomeric primary alcohol functional group.

In contrast to everything that has been done up until now, the amine functional group is carried by the sugar.

The corresponding bolaform acylating reagents were synthesized.

a) Synthesis of the acylating reagents

They are synthesized from 2 mercaptothiazoline and from acid dichloride containing a long alkane chain 8 according to the following scheme:

(16)

8

-continued 9  9a, n = 8
   9b, n = 10

The reaction is carried out in the presence of triethylamine in dichloromethane for 3 hours.

The acylating reagents are recrystallized and they exist in the form of a fluorescent powder.

The reaction yields are collated in the following table:

| Preparative yield of acylating reagents 9 | | |
|---|---|---|
| Acid dichloride | Derivatives | Yields (%) |
| 8a | 9a | 63 |
| 8b | 9b | 60 |

The acylating reagents were characterized by $H^1$ and $^{13}C$ NMR and microanalysis.

b) Synthesis of bolaforms

Glucosamine is commercially available in the hydrochloride form. It is thus dissolved in DMF in the presence of triethylamine. The acylating reagent is added to this solution.

The reaction scheme is the following:

(17)

10 bisglucosaminoalkanes

The reaction mixture is then stirred for 6h 30 at 70° C. and then for 17h 30 at room temperature. The bolaform compound 10 precipitates in the reaction mixture, it is filtered and then lyophilized.

The yields are combined in the following table: Preparative yields of bisglucosaminoalkanes 10

| Preparative yields of bisglucosaminoalkanes 10 | | |
|---|---|---|
| Acylating reagent | Derivatives | Yields (%) |
| 9a | 10a | 49 |
| 9b | 10b | 65 |

Procedure for the acylating reagents:

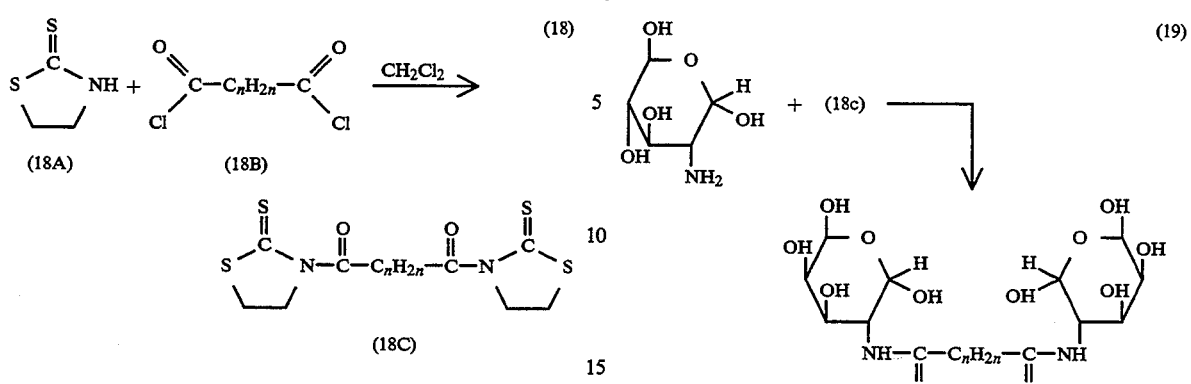

The thiazoline (35.4 mmol) is mixed with triethylamine (32.42 mmol) in 80 ml of dichloromethane.

Alkyl dichloride in solution in dichloromethane (19.25 mmol, 15 ml) is added dropwise to the above mixture. After all the dichloride has been,added, the reaction mixture is left stirring for 3 hours.

During reaction of the alkyl dichloride with the mercaptothiazoline, the solution becomes fluorescent yellow, which characterizes the formation of the acylating reagent.

The reaction mixture is then washed with a 0.5N hydrochloric acid solution and then with a 5% NaHCO$_3$ solution. The organic phase is then evaporated and the fluorescent yellow product is recrystallized from acetonitrile.

These compounds where characterized by microanalysis, H$^1$ NMR and C$^{13}$MR

Procedure for the bolaforms:

Glucosamine hydrochloride (4.65 mmol) is solubilized in dimethylformamide in the presence of triethylamine (5.11 mmol). The bolaform acylating reagent (2.35 mmol) is added to this solution.

The formation of the bolaform compound is followed by observing the disappearance of the fluorescent yellow coloration of the mixture. The reaction mixture is then stirred for 6h 30 at 70° C. and then for 17h 30 at room temperature.

A white precipitate is formed, according to the reaction scheme below, and the reaction mixture is then filtered and the product dried.

| Operating conditions and reaction yields in the synthesis of the bolaforms | | |
|---|---|---|
| Acylating reagent | Solvent | Yields (%) |
| 9a | 50 ml DMF | 66.5 |
| 9b | 100 ml DMF | 65 |

I-Dilactobioamidospermidines

Spermidine (1.35 mmol) is added to a solution containing 1 g of lactobionic acid (2.7 mmol), 25 ml of water and 25 ml of 2-propanol.

The reaction mixture is stirred for 24 h at room temperature.

The solvent is evaporated and the solid obtained is lyophilized.

1.2 g of hygroscopic product is obtained. This white solid has the formula:

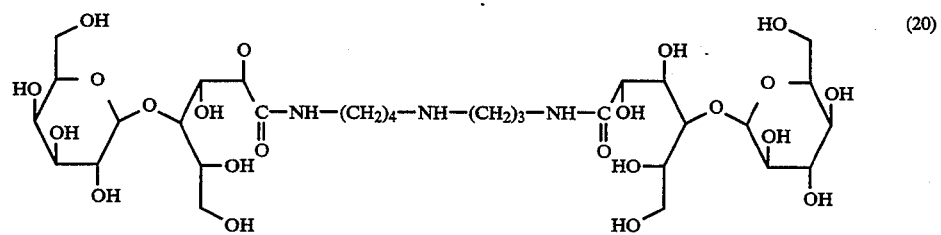

$C_{31}H_{59}N_3O_{22}$

These products were characterized by microanalysis, H$^1$ NMR and C$^{13}$ NMR.

II-Dilactobioamidospermines

Spermine (1.35 mmol) is added to a solution containing 1 g of lactobionic acid (2.7 mmol) and 100 ml of methanol.

The mixture is stirred for 24 hours. The solvent is evaporated and the white product is lyophilized.

1.325 g of white product is then obtained which is strongly hygroscopic, and its expanded formula is the following:

$$\text{(21)}$$

[Structure: bislactobionamide connected by —C(=O)—NH—(CH₂)₃—NH—(CH₂)₄—NH—(CH₂)₃—NH—C(=O)— linker with two lactobionic sugar units at each end]

$C_{34}H_{66}N_4O_{22}$

These products were characterized by microanalysis, H¹ [sic]NMR and C¹³ NMR.

III-Bisgluconamidodioxi or trioxoalkanes

The diamines containing oxygenated long chains have the formula:

$H_2N—(CH_2)_n—O—(CH_2)_h—O—(CH_2)_r)_s—NH_2$

They will be identified by the following code:

$n—O—m—O—p—(O—r)_s$

The oxygenated diamine (2.65 mmol) is added to the mixture containing gluconic acid (5.56 mmol) and 50 ml of solvent.

The mixture is stirred for 24 hours at room temperature. The product precipitates. It is then filtered and then lyophilized.

Solvents used and references of the products synthesized.

| Diamine | Solvent | Reference |
|---------|---------|-----------|
| 3O2O3   | methanol | G 3O2O3  |
| 3O6O3   | 2-propanol | G 3O6O3 |
| 3O2O2O3 | 2-propanol | G 3O2O2O3 |

General formula for bisgluconamidotrioxo[lacuna] or dioxoalkanes:

$$\text{(22)}$$

[Structure: gluconamide—NH—(CH₂)ₙ—O—(CH₂)ₙ—O—(CH₂)ₚ—(O—(CH₂)ᵣ)ₛ—NH—gluconamide]

All these products were characterized by microanalysis, H¹ NMR and C¹³ NMR.

IV-Bislactobionamidotrioxo[lacuna] or dioxoalkane bolaform compounds

The oxygenated diamine (1.35 mmol) is added to 1 g of lactobionic acid (2.7 mmol) in solution in 25 ml of water and 25 ml of 2-propanol.

The reaction mixture is then heated at 70° C. for 9h 30 and is then left stirring for 14h 30. The solvent is evaporated and the product is lyophilized.

The products obtained are strongly hygroscopic and have the following general formula:

$$\text{(23)}$$

[Structure: R-O-sugar—C(=O)—NH—(CH₂)ₙ—O—(CH₂)ₘ—O—(CH₂)ₚ—(O—(CH₂)ᵣ)ₛ—NH—C(=O)—sugar-O-R]

R = galactose

They are characterized by microanalysis, H¹ NMR and C¹³ NMR.

V-Bisaminolactose alkanes

The diamine (9.9 mmol), solubilized in 20 ml of propanol, is added to a solution of lactose (20.8 mmol) in 40 ml of water.

The mixture is then stirred at room temperature for 24 hours. It is then heated at 60° C. for 30'.

The solvent is evaporated and the solid is taken up in ethanol and toluene to remove traces of water. The product is-purified by recrystallization from ethanol.

The reaction yield is 70%.

VI-Bisgluconamidoalkane derivatives according to formula (I)

By convention, these bisgluconamidoalkanes will be denoted by the sequence n-n'-n, representing the methylene number.

a) Preparation of the 6-4-6 derivative 750 ml of methanol, then 9.8 g of 1.6 diaminohexane (84.2 mmol) and 6.2 g of adipic acid (42.1 mmol) are added to 15 g of δ-gluconolactone (84.2 mmol) weighed into a 1 liter, three-necked, round-bottomed flask.

The reaction mixture is stirred for 24 hours at 25° C. The reaction product precipitates; it is recovered by filtering on on a buchner and is then washed while hot with 3×100 ml of methanol at approximately 60° C.

The product is recovered in a crystallizing dish in order to be dried therein for 24 hours in a desiccator under vacuum. 26.5 g of the 6-4-6 derivative are recovered, i.e. an overall yield of 90%.

b) Preparation of the 6-10-6 derivative 750 ml of methanol, then 9.8 g of 1.6 diaminohexane (84.2 mmol) and 9.7 g of dodecanedioic acid (42.1 mmol) are added to 15 g of δ gluconolactone (84.2 mmol) weighed into a 1 liter, three-necked, roundbottomed flask.

The reaction mixture is added for 24 hours at 25° C. The reaction product precipitates; it is recovered by filtering on a buchner, and is then washed while hot with 3×100 ml of methanol at approximately 60° C.

The product is recovered in a crystallizing dish in order to be dried therein for 24 hours in a desiccator under vacuum. 29.5 g of the 6-10-6 derivative are recovered, i.e. an overall yield of 89.6%.

c) Preparation of the 2-10-2 derivative 750 ml of methanol, then 5 g of ethylenediamine (84.2 mmol) and 9.7 g of dodecanedinoic acid (42.1 mmol) are added to 15 g of of δ-gluconolactone (84.2 mmol) weighed into a 1 liter, three-necked, round-bottomed flask.

The reaction mixture is stirred for 24 hours at 25° C. The reaction product precipitates; it is recovered by filtering on a buchner, and is then washed while hot with 3×100 ml of methanol at approximately 60° C.

The product is recovered in a crystallizing dish in order to be dried therein for 24 hours in a desiccator under vacuum. 23.4 g of the 2-10-2 derivative are recovered, i.e. an overall yield of 83%.

We claim:

1. A compound of the formula

R A E A R wherein

E represents a linear or branched chain alkylene having at least 6 carbon atoms, a linear or branched chain dialkyl amino having at least 3 carbon atoms in each alkyl portion, or a linear or branched chain dialkyl ether having at least 3 carbon atoms in each alkyl portion;

A is a bonding group;

R represents a residue of a reducing glucide containing a linear or cyclized chain, or a derivative of a reducing glucide, where the residue is bonded directly or indirectly via one of its aldehyde or ketone groups, to the bonding group A.

2. A compound according to claim 1 wherein E represents a saturated carbon chain.

3. A compound according to claim 2, wherein E represents alkylene having from about 6 to 24 carbon atoms.

4. A compound according to claim 3, wherein E represents alkylene having from about 6 to 14 carbon atoms.

5. A compound according to claim 1 wherein the bonding group A is selected from the group consisting of oxygen,

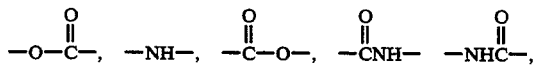

6. A compound according to claim 5, wherein the bonding functional group A is NH.

7. A compound according to claim 1, wherein the reducing glucide which forms the residue R is a monosaccharide.

8. A compound according to claim 7, wherein the residue R is selected from the group consisting of glucose and galactose.

9. A compound according to claim 1, wherein the reducing glucide which forms the residue R is a polysaccharide.

10. A compound according to claim 9, wherein the reducing glucide which forms the residue R is a disaccharide.

11. A compound according to claim 10, wherein the disaccharide is cellobiose, lactose or maltose.

12. A process for preparing a compound of the formula

R A E A R wherein E represents a linear or branched chain alkylene having at least 6 carbon atoms, a linear or branched chain dialkyl amino having at least 3 carbon atoms in each alkyl portion, or a linear or branched chain dialkyl ether having at least 3 carbon atoms in each alkyl portion;

A is a bonding group;

R represents a residue of a reducing glucide containing a linear or cyclized chain, or a derivative of a reducing glucide, where the residue is bonded directly or indirectly via one of its aldehyde or ketone groups, to the bonding group A.

comprising reacting an oxidized, reduced or aminated form of a reducing sugar with a compound of Formula BEB, where B corresponds to bonding group A prior to condensation with the sugar.

13. A process according to claim 12, wherein the reducing sugar is in the oxidized form.

14. A process according to claim 13, wherein the oxidized reducing sugar is a lactone or an acid.

15. A process according to claim 14, wherein the oxidized reducing sugar is gluconolactone.

16. A process according to claim 13, wherein the oxidized reducing sugar is lactobionic acid.

* * * * *